United States Patent [19]

Wypych

[11] Patent Number: 5,199,943
[45] Date of Patent: Apr. 6, 1993

[54] ULTRASONIC SURGICAL HANDPIECE

[75] Inventor: Peter Wypych, Irvine, Calif.

[73] Assignee: Alcon Surgical, Inc., Fort Worth, Tex.

[21] Appl. No.: 806,566

[22] Filed: Dec. 12, 1991

[51] Int. Cl.⁵ .......................................... A61B 17/00
[52] U.S. Cl. ...................................... 604/22; 606/169; 606/107
[58] Field of Search .................. 604/22; 606/128, 169, 606/107; 128/24 AA

[56] References Cited

U.S. PATENT DOCUMENTS

| | | |
|---|---|---|
| 3,589,363 | 6/1971 | Banko . |
| 3,693,613 | 9/1972 | Kelman . |
| 4,180,074 | 12/1979 | Murry et al. . |
| 4,223,676 | 9/1980 | Wuchinich et al. . |
| 4,428,748 | 1/1984 | Peyman et al. . |
| 4,515,583 | 5/1985 | Sorich . |
| 4,573,979 | 3/1986 | Blake . |
| 4,578,059 | 3/1986 | Fabricant et al. . |
| 4,609,368 | 9/1986 | Dotson . |
| 4,634,420 | 1/1987 | Spinosa et al. . |
| 4,643,717 | 2/1987 | Cook et al. ............... 606/169 |
| 4,652,255 | 3/1987 | Martinez . |
| 4,681,561 | 7/1987 | Hood et al. . |
| 4,705,500 | 11/1987 | Reimels et al. . |
| 4,787,889 | 11/1988 | Steppe et al. . |
| 4,804,364 | 2/1989 | Dieras et al. ............. 606/169 |
| 4,808,154 | 2/1989 | Freeman . |
| 4,816,017 | 3/1989 | Hood et al. . |
| 4,816,018 | 3/1989 | Parisi . |
| 4,869,715 | 9/1989 | Sherburne . |
| 4,886,060 | 12/1989 | Wiksell ........................ 604/22 |
| 4,922,902 | 5/1990 | Wuchinich et al. . |
| 4,983,160 | 1/1991 | Steppe et al. . |
| 5,058,570 | 10/1991 | Idemoto et al. ............. 604/22 |
| 5,123,903 | 6/1992 | Quaid et al. ............... 606/169 |
| 5,151,084 | 9/1992 | Khek ........................... 606/169 |

FOREIGN PATENT DOCUMENTS

| | | | |
|---|---|---|---|
| 3826414 | 2/1989 | Fed. Rep. of Germany ...... 606/128 |
| 8803783 | 6/1988 | PCT Int'l Appl. ........... 128/24 AA |

Primary Examiner—Ralph Lewis
Attorney, Agent, or Firm—Jeffrey S. Schira

[57] ABSTRACT

An ultrasonic surgical handpiece having a generally hollow body with a reduced diameter portion at a free end and an interior surface, an ultrasonic horn coaxially mounted inside the body, terminating at the free end and defining a fluid flow passage at the reduced diameter portion and a spiral thread formed in the interior surface at the reduced diameter portion for reducing shearing of a fluid flowing through the fluid flow passage created by an ultrasonic vibration of the horn.

4 Claims, 3 Drawing Sheets

ULTRASONIC SURGICAL HANDPIECE

BACKGROUND OF THE INVENTION

The present invention relates to ultrasonic surgical equipment and, in particular, to ultrasonic surgical handpieces, resonating bars or horns and related ultrasonic cutting tips. Ultrasonic surgical handpieces, resonating bars or horns and related ultrasonic cutting tips are the critical and principal parts of ultrasonic surgical equipment.

A typical ultrasonic surgical device consists of an ultrasonically driven handpiece with attached cutting tip and irrigating sleeve and an electronic control console. The handpiece assembly or probe is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezo-electric crystals. The crystals supply the required ultrasonic vibrations needed to drive both the horn and the attached cutting tip during surgery and are controlled by the console. The crystal/horn assembly is suspended within the hollow body or shell of the handpiece by flexible mountings. The handpiece body terminates in a reduced-diameter portion or nosecone at the body's distal end. The nosecone is externally threaded to accept the irrigation sleeve. The horn has a bore that is internally threaded at its distal end to receive the cutting tip. The irrigation sleeve also has an internally threaded bore that is screwed onto the external thread of the nosecone. The cutting tip and sleeve are sized so that the tip projects only a predetermined amount past the open end of the irrigating sleeve. Ultrasonic surgical instruments, cutting tips and irrigating sleeves are more fully described in U.S. Pat. Nos. 3,589,363, 3,693,613, 4,180,074, 4,223,676, 4,515,583, 4,573,979, 4,578,059, 4,609,368, 4,634,420, 4,643,717, 4,652,255, 4,681,561, 4,705,500, 4,787,889, 4,808,154, 4,816,017, 4,816,018, 4,869,715, 4,922,902 and 4,983,160, the entire contents of which are incorporated herein by reference.

In use, the ends of the cutting tip and irrigating sleeve are inserted into a small incision of predetermined size in the cornea, or other surgical site. The cutting tip is ultrasonically vibrated within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the surgical site through the open end of the cutting tip, the cutting tip and horn bores, and the aspiration line into a collection device on the console. The aspiration of emulsified tissue is aided by a saline flushing solution or irrigant that is injected into the surgical site through the small annular gap between the inside surface of the irrigating sleeve and the cutting tip and by ports at the distal end of the sleeve.

As discussed in U.S. Pat. Nos. 4,681,561 and 4,816,017 to Hood, et al., one desirable characteristic of ultrasonic handpieces is consistent, linear power delivery to the cutting tip over the entire power band. Power surges and drop offs are undesirable, particularly during microsurgery in the eye. Most prior art surgical handpieces exhibit linear power delivery over the upper two-thirds of their power band. However, in the lower portion of the power band, many prior art handpieces do not exhibit linear power delivery. As a result, as the surgeon slowly increases the power to the piezo-electric crystal in the handpiece at the lower end of the power band from an off position, few if any of the crystal vibrations are transmitted longitudinally down the cutting tip shaft to the distal end of the cutting tip until some minimum power level is reached, at which point the distal end of the cutting tip suddenly begins to vibrate. Correspondingly, as the power to the piezo-electric crystal is slowly reduced from above to below this minimal point, the ultrasonic vibrations at the distal end of the cutting tip abruptly stop. As a consequence, control of the handpiece at the lower portion of the power band below this minimal power level is lost, thereby decreasing the usable power band of the handpiece and introducing power surges and drop offs.

This phenomenon never has been explained fully in the prior art. For example, in their U.S. Pat. Nos. 4,681,561 and 4,816,017, Hood, et al. disclose that the presence of cavitation bubbles has an effect on the stability of the surgical handpiece by creating variations in the mechanical impedance in the handpiece that cause corresponding variations in the mechanical operating characteristics of the handpiece. The decoupling sleeve disclosed in these patents serves to reduce these variation by isolating the handpiece shell from the cutting tip. While this decoupling sleeve is extremely efficient at reducing cavitation bubbles and minimizes power surges and drop offs, the sleeve must be manually installed on the handpiece and discarded after each use, adding extra work and expense to the surgical procedure. Accordingly, a need continues to exist for an ultrasonic handpiece that has inherent linear power delivery and does not require the use of external stabilizing devices.

BRIEF SUMMARY OF THE INVENTION

The ultrasonic handpiece of the present invention improves upon prior art handpiece by providing a handpiece having an internally threaded nosecone. The inventor has discovered that the narrow, annular irrigation fluid passage between the interior of the nosecone and the ultrasonic horn induces laminar flow in the irrigation fluid. The laminar nature of the fluid flow causes the horn to shear the fluid as the fluid passes around the vibrating horn, robbing power from the horn. These shear losses in the horn must first be overcome before the ultrasonic vibrations of the horn can be transmitted to the cutting tip. The threshold point of power surge and power drop off corresponds to the point at which the fluid is sheared and the vibrations of the horn begins to be transmitted to the cutting tip. This threshold point will vary with the shear resistance or viscosity of the fluid (i.e. lower in low viscosity fluids and higher in high viscosity fluids).

This shearing of the irrigation fluid is possible because of the thin cross section and laminar flow of the irrigation fluid as it passes between the handpiece shell and the horn. If the laminar flow can be disrupted or made turbulent, shearing of the fluid will be reduced, thereby lowering the power threshold point of the handpiece to nearly zero and resulting in near linear power delivery across the entire power band. The internally threaded nosecone of the present invention creates eddies in the fluid flow, thereby eliminating the laminar nature of the flow stream and reducing the shear losses of the horn.

Accordingly, one objective of the present invention is to provide an ultrasonic surgical handpiece having linear power delivery.

A further objective of the present invention is to provide an ultrasonic surgical handpiece that minimizes shearing of the irrigation fluid.

Another objective of the present invention is to provide an ultrasonic surgical handpiece having an internally threaded nosecone.

Still another objective of the present invention is to provide an ultrasonic surgical handpiece that induces turbulent flow in the irrigation fluid.

These and other objectives and advantages of the present invention will become apparent from the drawings, detailed description and claims which follow.

DETAILED DESCRIPTION OF THE INVENTION

Figure 1:
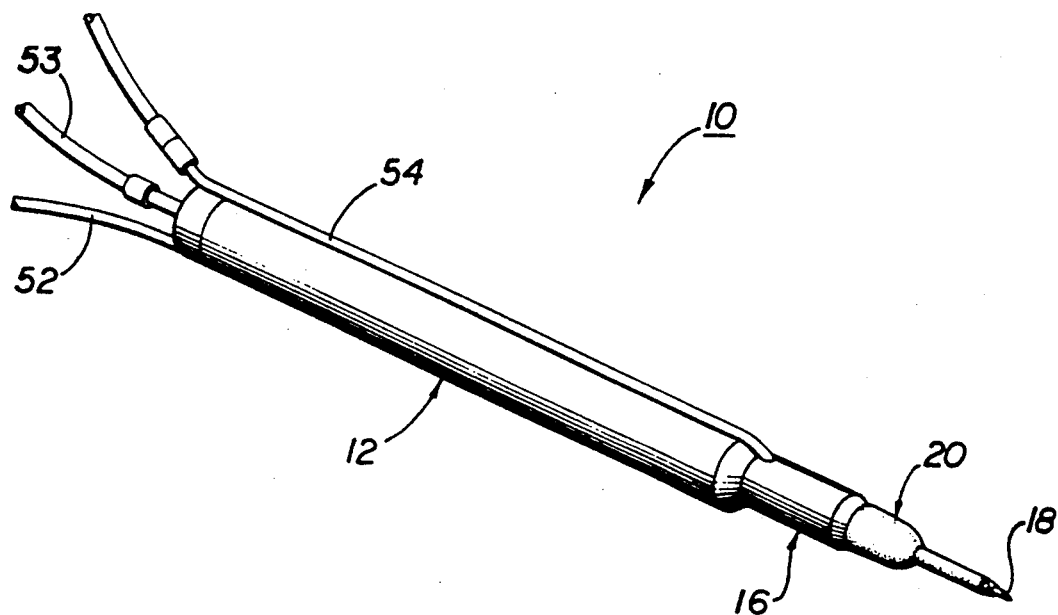
FIG. 1 is a perspective view of a phacoemulsification handpiece incorporating the present invention.
Figure 2:
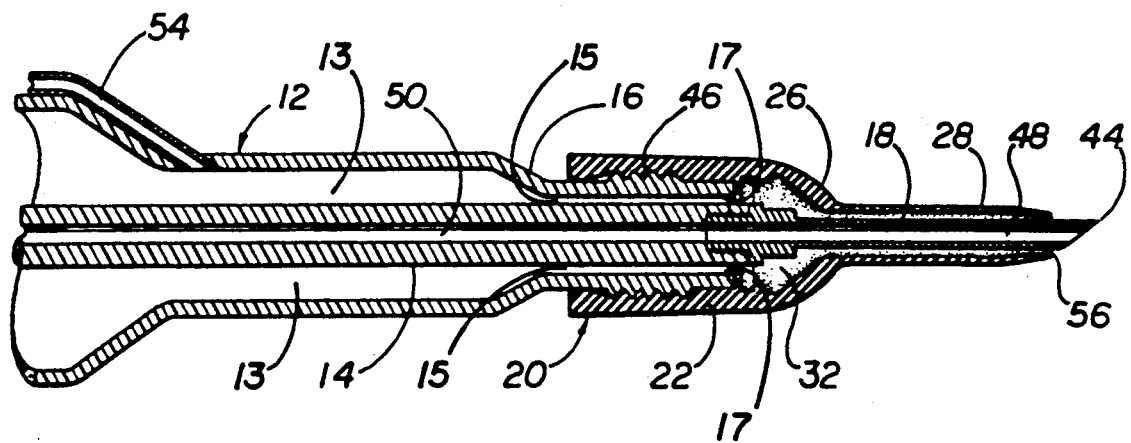
FIG. 2 is an enlarged longitudinal cross section of the distal end of a prior art handpiece assembly similar to that illustrated in FIG. 1.

As can be seen in FIGS. 1 and 2, handpiece assembly 10 generally comprises a hollow handpiece shell or body 12 having an integrally formed handpiece nosecone 16, an ultrasonically driven horn 14, an electric power supply cord 52, an aspiration line 53, an integral irrigation line 54, a hollow surgical cutting tip 18 and an irrigating sleeve 20. Horn 14, cutting tip 18 and irrigating sleeve 20 are known in the art and are available from manufacturers such as Alcon Surgical, Inc. and others. Body 12 is preferably titanium or stainless steel, but other suitable materials may also be used.

Handpiece assembly 10 is assembled by threading cutting tip 18 on horn 14 in handpiece body 12. Sleeve 20 is telescopically inserted over cutting tip 18 so that distal tip end 44 of cutting tip 18 extends through bore 30 and projects a predetermined distance out free end 34 of tube 28 and internal threads 24 in hollow interior 32 of base 22 are received on external threads 46 on nosecone 16. Handpiece assembly 10 is connected to any suitable conventional control panel (not shown) such as the Series Ten Thousand Master Phacoemulsifier ™ available from Alcon Surgical, Inc., Fort Worth, Texas.

In use, horn 14 is caused to vibrate ultrasonically and these vibrations are transmitted longitudinally along cutting tip 18 to distal tip end 44 where the vibrations are used to fracture or emulsify tissue (not shown). A reduced pressure source (not shown) draws the emulsified tissue or aspirant through bore 48 in cutting tip 18 and bore 50 in horn 14 and out handpiece assembly 10 through flexible aspiration line 53. An irrigant source (not shown) supplies an irrigant such as saline solution under pressure through irrigation line 54 and handpiece body 12 to the interior 32 of sleeve base 22 where the irrigant is forced to migrate along bore 30 in tube 28 through annular space 56 between cutting tip 18 and interior surface 38 of tube 28. The irrigant exits handpiece assembly 10 out free end 34 of tube 28 and out ports 36.

As can be seen in FIG. 2, horn 14 coaxially extends through reduced diameter bore 15 in nosecone 16 of prior art handpiece 12. Bore 15 has smooth interior surface 17. Irrigation fluid flowing around horn 14 within interior 13 of body 12 is forced through bore 15 in the annular space between horn 14 and smooth surface 17 into interior 32 of sleeve 20 and out distal end 44 through annular space 56 between cutting tip 18 and interior surface 38 of tube 28. As the irrigation fluid flows through the narrow passage between surface 17 and horn 14, the fluid flow is laminar. Therefore, the longitudinal vibrations of horn 14 within bore 15 are resisted by the viscosity of the irrigation fluid. These vibrations can be transmitted to distal end 44 through cutting tip 18 only after the shear resistance of the irrigation fluid is overcome.

Figure 3:
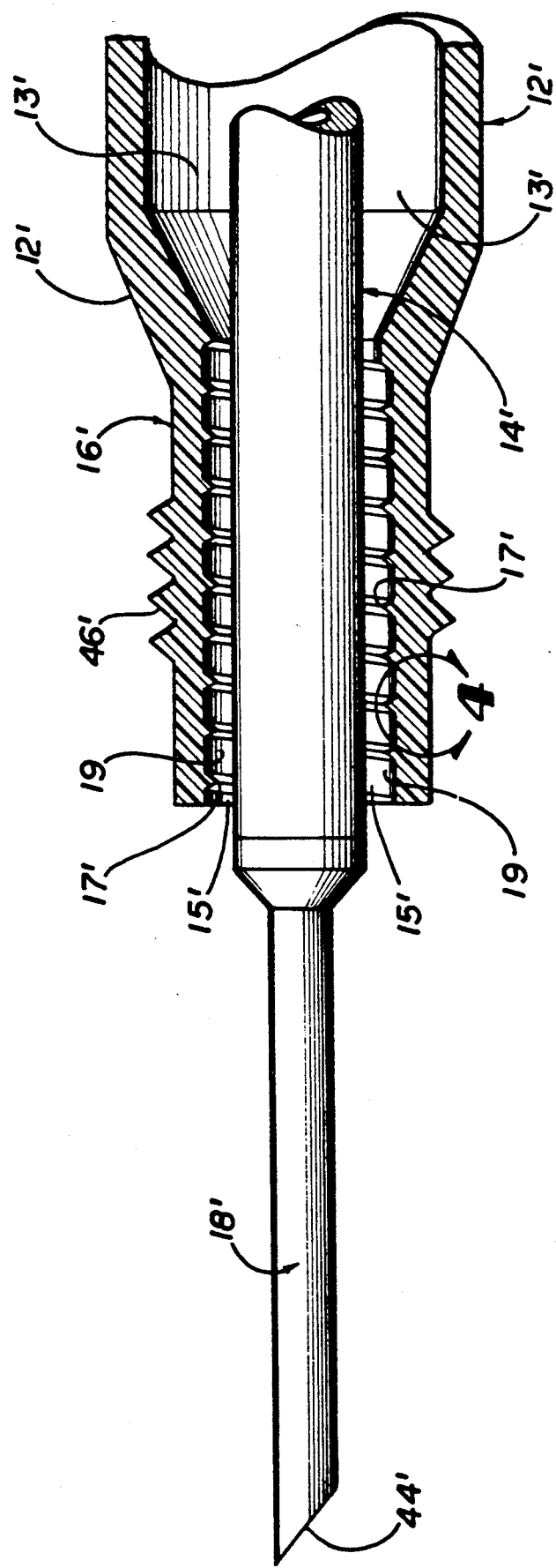
FIG. 3 is an enlarged fragmentary longitudinal cross section of the handpiece assembly of the present invention shown in FIG. 1 with the cap sleeve removed.
Figure 4A:
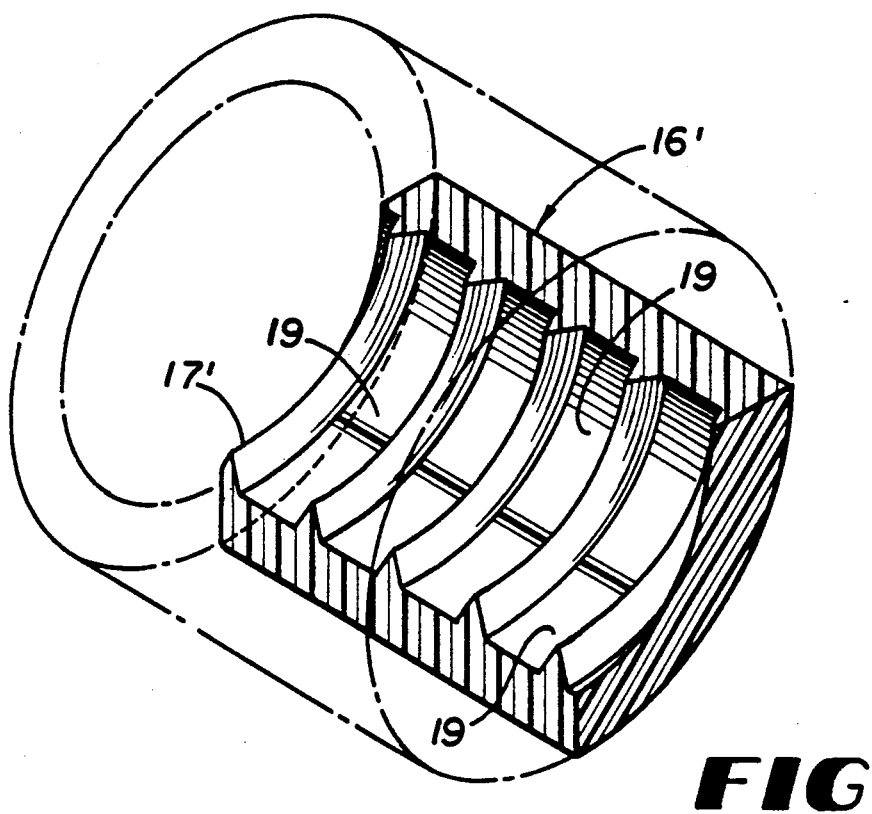
FIGS. 4A-4B are enlarged fragmentary perspective views of two embodiments of the present invention on the interior surface of the handpiece nosecone illustrated in FIG. 3 taken at circle 4.
Figure 4B:
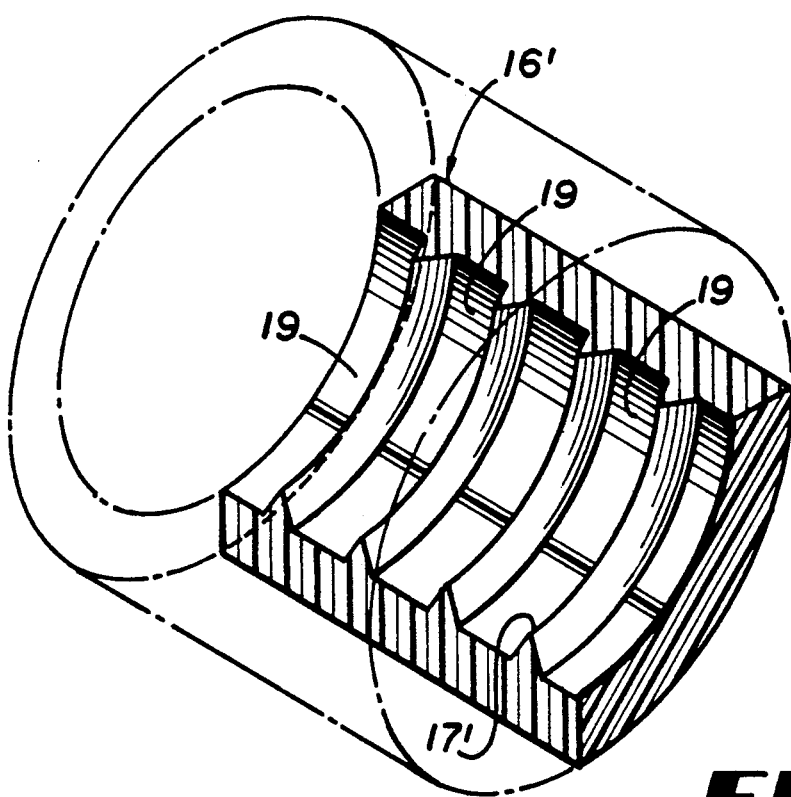

As can be seen in FIGS. 3, 4A and 4B, surface 17' of the present invention contains grooves 19. Grooves 19 preferably are formed as a single spiral thread, as illustrated in FIG. 4A, or as a series of spaced, concentric rings, as illustrated in FIG. 4B, but any suitable groove profile and construction may also be used. Preferably, nosecone 16' has grooves 19 covering approximately between 20 percent and 100 percent of interior surface 17' and cut approximately between 0.005 inches and 0.015 inches into surface 17'. Grooves 19 are preferably lathed or tapped into nosecone 16' during manufacture but other suitable methods of forming grooves 19 in nosecone 16' may also be used.

As can be seen in FIG. 3, in use, the irrigation fluid flows longitudinally along horn 14' within interior 13'. As the irrigation fluid enters reduced diameter bore 15' and flows within grooves 19, eddies are formed in the flow stream creating turbulence. The turbulence of the irrigation fluid flow significantly reduces the shear losses of horn 14' as it vibrates within bore 15'. The energy losses within the irrigation fluid flow stream caused by the induced turbulent flow are not critical and can be overcome by increasing the pressure of the irrigation fluid.

This description is given for purposes of illustration and explanation. It will be apparent to those skilled in the relevant art that modifications can be made to the invention as described above without departing from its scope or spirit.

I claim:

1. An ultrasonic surgical handpiece, comprising:
   a) a generally rigid, hollow body having a reduced diameter portion at a free end and an interior surface;
   b) an ultrasonic piezo-electric horn coaxially mounted inside the body, terminating at the free end and defining a fluid flow passage between the horn and the interior surface of the body at the reduced diameter portion; and
   c) a spiral thread formed in the interior surface at the reduced diameter portion for reducing shearing created by ultrasonic vibration of the horn of a fluid flowing through the fluid flow passage.

2. An ultrasonic surgical handpiece, comprising:

a) a generally rigid, hollow body having a reduced diameter portion at a free end and an interior surface;
b) an ultrasonic piezo-electric horn coaxially mounted inside the body, terminating at the free end and defining a fluid flow passage between the horn and the interior surface of the body at the reduced diameter portion; and
c) a plurality of spaced, concentric rings formed in the interior surface at the reduced diameter portion for reducing shearing created by ultrasonic vibration of the horn of a fluid flowing through the fluid flow passage.

3. An ultrasonic surgical handpiece, comprising:
a) a generally rigid, hollow, stainless steel body having a reduced diameter portion at a free end and an interior surface;
b) an ultrasonic piezo-electric horn having a bore coaxially mounted inside the body, the horn terminating at the free end and defining a fluid flow passage between the horn and the interior surface of the body at the reduced
c) a spiral thread formed in the interior surface at the reduced diameter portion for reducing shearing created by ultrasonic vibration of the horn of a fluid flowing through the fluid flow passage.

4. An ultrasonic surgical handpiece, comprising:
a) a generally rigid, hollow, stainless steel body having a reduced diameter portion at a free end and an interior surface;
b) an ultrasonic piezo-electric horn having a bore coaxially mounted inside the body, the horn terminating at the free end and defining a fluid flow passage between the horn and the interior surface of the body at the reduced diameter portion; and
c) a plurality of spaced, concentric rings formed in the interior surface at the reduced diameter portion for reducing shearing created by ultrasonic vibration of the horn of a fluid flowing through the fluid flow passage.

* * * * *